US005549665A

United States Patent [19]
Vesely et al.

[11] Patent Number: 5,549,665
[45] Date of Patent: Aug. 27, 1996

[54] BIOPROSTETHIC VALVE

[75] Inventors: Ivan Vesely; Slawomir Krucinski; Gordon Campbell; Derek Boughner; Mohan Dokainish, all of London, Canada

[73] Assignee: London Health Association, London, Canada

[21] Appl. No.: 261,983

[22] Filed: Jun. 17, 1994

[30] Foreign Application Priority Data

Jun. 18, 1993 [GB] United Kingdom ............ 9312666

[51] Int. Cl.$^6$ ..................................... A61F 2/24
[52] U.S. Cl. ............................. 623/2; 623/900
[58] Field of Search ................... 623/2, 66, 900

[56] References Cited

U.S. PATENT DOCUMENTS

| | | | |
|---|---|---|---|
| 4,259,753 | 4/1981 | Liotta et al. | 623/2 |
| 4,725,274 | 2/1988 | Lane et al. | 623/2 |
| 4,851,000 | 7/1989 | Gupta | 623/2 |
| 5,163,953 | 11/1992 | Vince | 623/2 |
| 5,258,023 | 11/1993 | Reger. | |
| 5,326,370 | 7/1994 | Love et al. | 623/2 |

FOREIGN PATENT DOCUMENTS

| | | | |
|---|---|---|---|
| 220097 | 3/1987 | European Pat. Off. | 623/2 |
| 8300617 | 3/1983 | WIPO | 623/2 |
| WO94/01060 | 1/1994 | WIPO. | |

OTHER PUBLICATIONS

"Numerical Simulation of Leaflet Flexure in Bioprosthetic Valves Mounted on Rigid and Expansile Stents," 28 Dec. 1992, by S. Krucinski, I. Veley, M. A. Dokainish, and G. Campbell.

"Pivoting Stent Posts Reduce Stresses in Pericardial Bioprosthetic Valves: A Numerical Analysis," by I. Vesely and S. Krucinski.

Primary Examiner—Michael Milano
Attorney, Agent, or Firm—Fay, Sharpe, Beall, Fagan, Minnich & McKee

[57] ABSTRACT

A bioprosthetic valve comprising a support ring having three spaced apart end stops projecting upwardly therefrom, a stent post ring having three spaced apart stent posts pivotally connected thereto and adapted to engage respective ones of the end stops so as to permit outward pivoting of the stent posts and to prevent inward pivoting thereof, a leaflet valve having three generally triangular leaflets defining respective cusps, the leaflets being joined at respective commissures, and a sewing ring for attaching the leaflet valve to the stent post ring and support ring.

21 Claims, 4 Drawing Sheets

BIOPROSTETHIC VALVE

FIELD OF THE INVENTION

This invention relates in general to bioprosthetic valves, and more particularly to a novel bioprosthetic heart valve with pivoting supporting stent posts for holding valve leaflets therebetween.

BACKGROUND OF THE INVENTION

When a patient's own heart valve becomes diseased, it can be either repaired or surgically replaced with an artificial valve. There are two basic types of artificial heart valves, mechanical valves and tissue valves. Mechanical valves are made of metal or hard plastic, whereas tissue valves consist of chemically preserved animal tissue, usually extracted from pig (porcine) or cow (bovine). The animal tissue valves are mounted on a supporting frame or "stent". The stent enables the surgeon to insert and mount the valve into the heart with minimal difficulty. The stents themselves are constructed from a polymer material and are covered with DACRON® cloth that contains a sewing ring. Typically, three stent posts project upwardly from the sewing ring and hold the three valve leaflets suspended in the required geometry.

Animal tissue valves have some inherent advantages over mechanical valves since they do not require the patient to be on chronic anticoagulants. Unfortunately, tissue valves eventually suffer from failure in a manner similar to human heart valves, and therefore need periodic replacement. Currently, the survival rate of bioprosthetic tissue valves is approximately 95% after five years from surgery, but only 40% after fifteen years from surgery.

The failure of these animal tissue valves results from poor mechanical properties. Specifically, the supporting stents are relatively rigid, and cannot mimic the cyclic expansion and contraction of the natural aorta where the valve sits. It is believed that mounting of the valves on such non-physiological stents contributes to mechanical damage caused by repetitive sharp bending at the stent posts. Much of the damage to the valve tissue occurs during valve opening because the supporting stents cannot dilate with the recipient's aorta. Such unnatural behaviour induces sharp curvatures within the leaflets and very high local stresses that damage the leaflet material and ultimately cause it to fail through flexural fatigue.

The inventors have recognized the desirability of providing a bioprosthetic heart valve with a flexible or expansive supporting stent. In Krucinski S., Yesely I., Dokainish M. A., Campbell G. "Numerical Simulation of Leaflet Flexure in Bioprosthetic Valves Mounted on Rigid and Expansile Stents", Journal of Biomechanics (26(8):929–943, 1993), the inventors describe a simulated stent with posts that pivot about their respective bases for reducing compressive commissural stressing in a bioprosthetic heart valve. Also, in pivoting stent posts reduce flexural stresses in pericardial bioprosthetic valves: A numerical analysis, presented at the 1993 conference of ASAIO, New Orleans, May, 1993 the concept of pivoting stents was disclosed.

Another prior art bioprosthetic valve is disclosed in U.S. Pat. No. 5,258,023 (Reger). This valve incorporates a stent comprising a frame which is fully covered by a biochemically inert or physiologically compatible shroud. The frame is in the form of a hollow cylinder of rectangular cross-section which is machined or trimmed to provide a suturing support ring, extended cusp stanchions, and interference free blood flow to the coronary arteries. The frame is joint free but is made slightly deformable to conform to contractile changes of the heart. The Reger Patent discloses that such deformity and expansion permits the frame to compliantly respond to expansion and contraction of the native valve orifice of the beating heart in which the aortic valve is implanted in order to reduce beat-by-beat stress on the aortic valve and anchoring sutures, thereby reducing the likelihood of eventual valve dehiscence.

As indicated above, the inventors have realized that while outward movement of the stent posts reduces local stresses on the leaflet material, it is also extremely important to limit the inward movement of the stent posts in order to reduce compressive flexural stresses on the valve leaflets.

Accordingly, although the provision of flexible stent posts is known in the prior art, no practical heart valve has yet been provided for allowing limited outward movement of the stent posts during systole while also preventing inward movement of the stent posts during diastole so as to reduce commissural stresses in the valve leaflets.

Moreover, the inventors' mathematical modelling (see J. Biomechanics article discussed above) has shown that a compliant supporting frame cannot deform sufficiently outward to enable the required amount of expansion to reduce stresses, and still provide structural rigidity to prevent collapse of the frame inward during valve closure.

SUMMARY OF THE INVENTION

According to the present invention, a bioprosthetic valve is provided with a plurality of pivoting stents for supporting the valve leaflets or cusps. According to the preferred embodiment, the bioprosthetic valve of the present invention is used as a replacement for the human heart valve, although the valve of the present invention may be used to replace other valves in the human body with only minor modifications in design and size. In the preferred heart valve embodiment, the tips of the stents are attached to the aortic wall, which causes outward pivoting as the aorta expands during systole, to facilitate significant reduction of local stresses in the valve leaflets. The valve also includes end stops for preventing the stents from moving excessively inward during diastole and ensuring a properly functioning valve that seals well. A truly, freely pivoting frame with inward acting end stops provides both unrestricted outward movement, and controlled inward rigidity. Thus, the bioprosthetic heart valve according to the present invention provides a more natural opening for the valve leaflets and reduces leaflet bending and the associated stresses which are characteristic of prior art heart valves.

BRIEF DESCRIPTION OF THE DRAWINGS

A description of the prior art and of the preferred embodiment of the present invention is provided in greater detail below with reference to the following drawings, in which.

Figure 1:
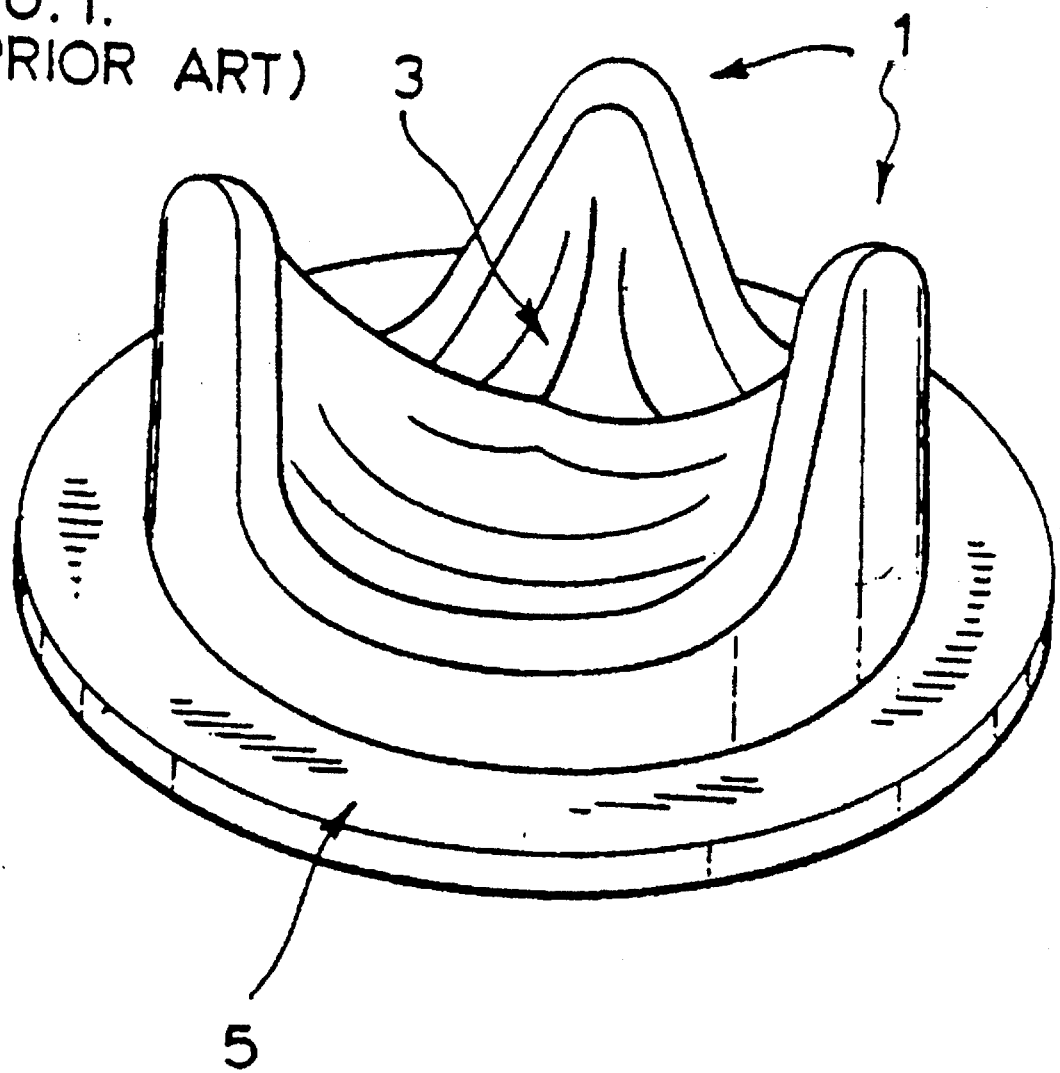
FIG. 1 is a perspective view of a prior art bioprosthetic heart valve.
Figure 2:
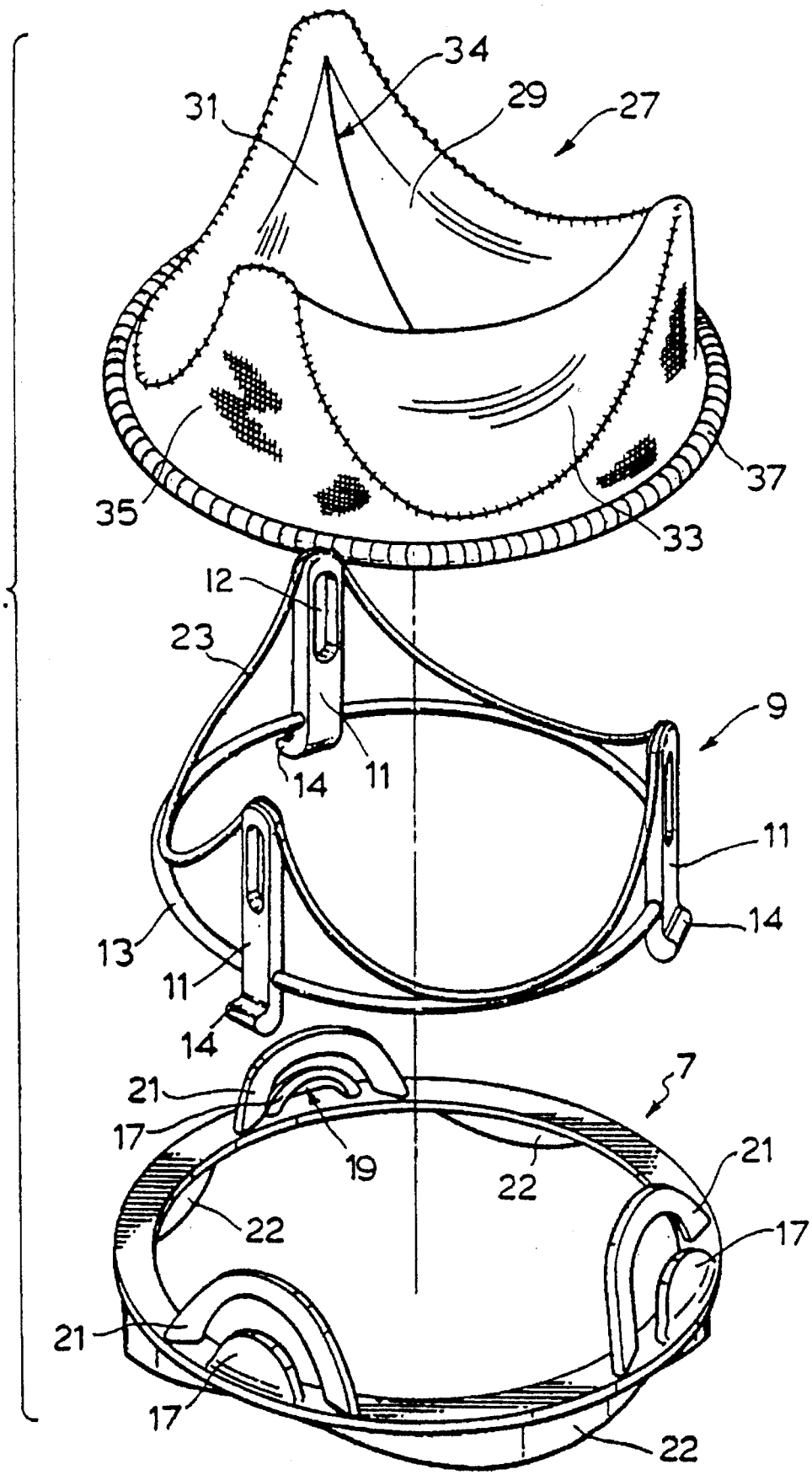
FIG. 2 is an exploded perspective view of the bioprosthetic heart valve according to the preferred embodiment of the present invention.

DETAILED DESCRIPTION OF THE INVENTION AND PRIOR ART with reference to FIG. 1, a prior art bioprosthetic valve (e.g. pig aortic valve or calf pericardium) is shown mounted to a rigid support frame with stent posts 1 projecting upwardly from a sewing ring 5, so that the valve leaflets meet to form cusps 3 through which blood is intended to flow. While some prior art frames or stents claim to be flexible, such as disclosed in U.S. Pat. No. 5,258,023 (Reger), the posts 1 in prior art devices have been found to flex only inward during valve closure. Since the base of each stent post 1 has a fixed diameter the stent posts generally do not move outward during systolic valve opening.

In contrast, the natural aortic root expands considerably during valve opening. Medical studies have shown that proper functioning of the aortic valve depends on aortic root expansion. The natural expansion of the aortic root at the onset of systole enables the commissures to move apart, and initiate the opening of the aortic valve. When the root is fully expanded, the free edge of the leaflet in a natural aortic valve is pulled taught between the commissures creating a rough triangular shaped orifice for the majority of systole. The slight tension on the leaflets in systole eliminates compressive stresses and minimizes circumferential bending.

Prior art stented bioprosthetic valves such as shown in FIG. 1, by virtue of their design, cannot expand in systole. The valve opens through central reverse flexing, and the leaflets often experience sharp bends and very high curvatures which eventually lead to valve failure.

Turning now to the preferred embodiment of the invention, a bioprosthetic heart valve is shown in FIGS. 2–5. The valve comprises a preferably rigid support ring 7 into which a flexible stent post ring 9 is inserted for snap-fit engagement. The stent post ring 9 is preferably fabricated from a suitable flexible polymer and includes a plurality of stent posts 11 interconnected via a connecting brace 13. Each of the stent posts 11 comprises a main body portion which, according to the illustrated preferred embodiment, is generally flat, although in alternative embodiments may be of variable cross-section. The stent post main body portions are connected to the connecting brace 13 adjacent a lower end of each stent post as shown in detail with reference to FIG. 5. The lower end of each stent post 11 has an outward protrusion 14, the purpose of which is discussed in greater detail below. Each stent post has an oblong hole 12 extending therethrough to facilitate attachment of tissue and/or cloth covering by suturing.

The support ring 7 includes three end stops. Each end stop comprises a first member 17 projecting upwardly from an outer diameter of the support ring and being of generally spherical segment shape defining a hollow internal portion 19. Each of the end stops also comprises a second member 21 projecting from the outer diameter of the support ring toward an inner diameter of the support ring in the form of an arch. The support ring 7 further includes a scalloped extension 22 from the bottom surface thereof which is adapted to conform to the correct geometry of the aortic root.

Figure 3:
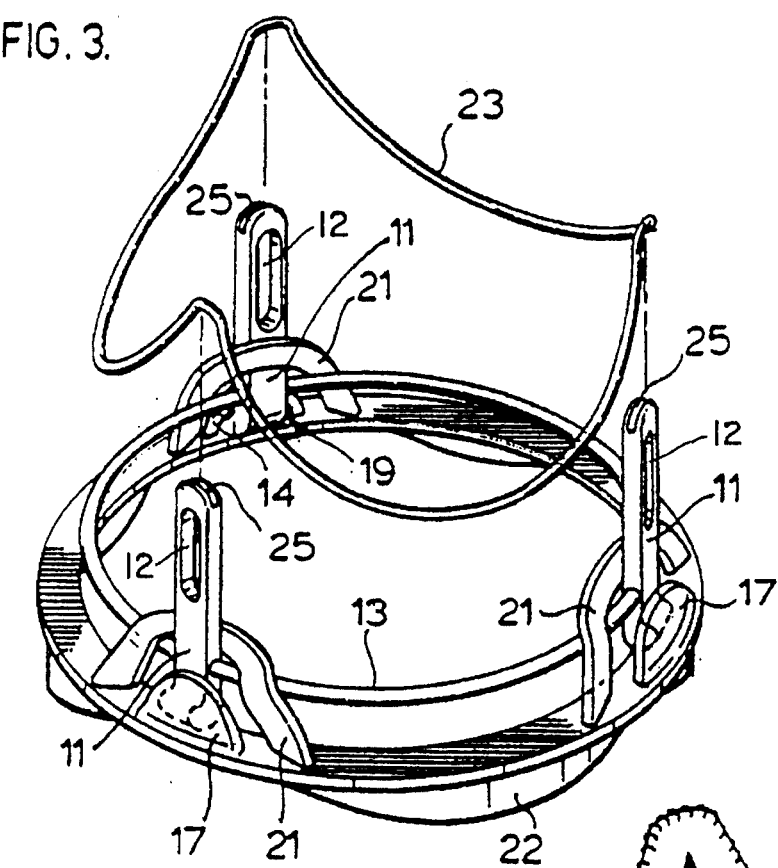
FIG. 3 shows connection of a leaflet cusp supporting wire frame to individual stent posts of the heart valve shown in FIG. 2.
Figure 5:
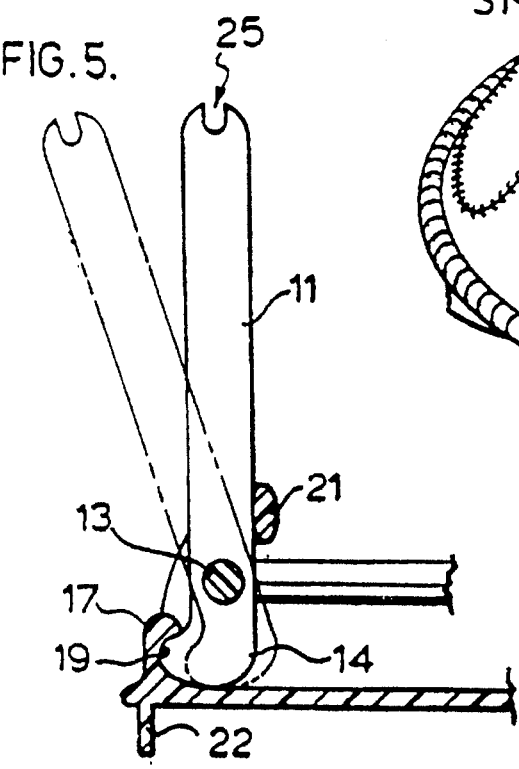
FIG. 5 is a detailed cross-sectional view showing pivoting of the stent posts in the heart valve of the preferred embodiment.

During assembly, as shown best with reference to FIGS. 3 and 5, the upper distal ends of stent posts 11 are inserted through the support ring 7 from beneath and then are moved further upwardly through the opening between end stop first member 17 and second member 21 until protrusion 14 hooks into the hollow internal portion 19 of the first member 17, thereby completing the snap-fit engagement of the stent post ring 9 to the support ring 7.

Next, a wire frame 23 is received in a slot 25 disposed in the upper distal end of each stent post 11.

Finally, the animal leaflet valve 27 is placed over the support ring 7, stent post ring 9 and wire frame 23. As discussed above, the animal tissue leaflet valve 27 typically comprises a pig aortic valve or calf pericardium defining three leaflets 29, 31 and 33, to which a cloth cover 35 is sewn. The cloth cover 35 may be sewn into either or both of the leaflet valve 27 or stent posts 11, with the stent posts 11 being covered both inside and out. As in the prior art, the valve leaflets 29, 31 and 33 meet to define respective cusps (such as cusp 34) which open and close during systole and diastole, respectively. A soft sewing ring 37 is provided at the base of the animal tissue valve 27 by which the animal tissue valve 27 may be sewn to the support ring 7, as shown best with reference to FIG. 4.

Figure 4:
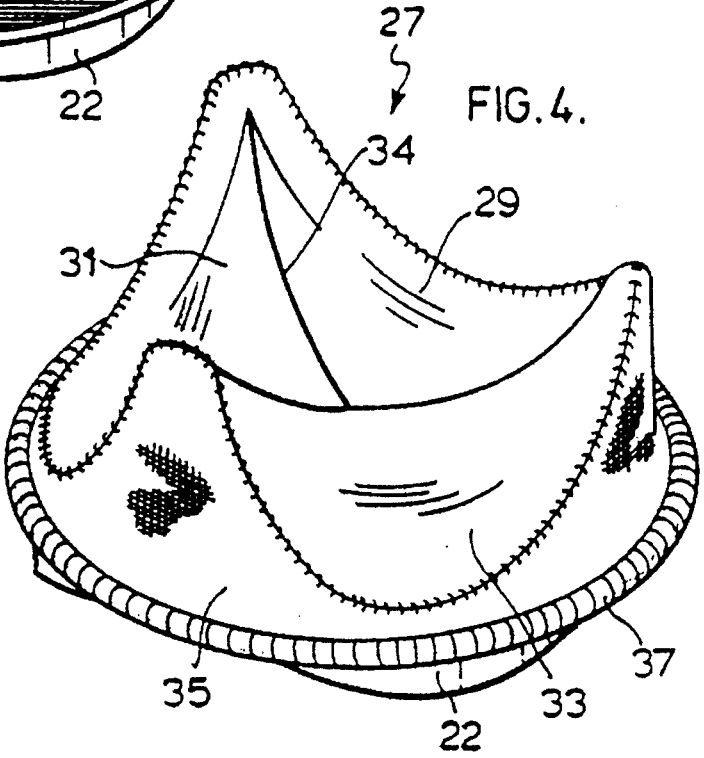
FIG. 4 is a perspective view of an assembled heart valve according to the preferred embodiment.

In the assembled form shown in FIG. 4, the wire frame 23 (FIGS. 2 and 3) provide support for the leaflet valve 27 on the stent post ring 9.

As shown best with reference to FIG. 5, the bottom portion of each stent post 11 is adapted to slide along the support ring 7 during pivoting in systole (shown in phantom) and to hook inside the hollow internal portion 19 during diastole (solid lines). Furthermore, a portion of the main body of the stent post 11 abuts the second member 21 above the pivot point provided by connecting brace 13 during diastole, further limiting the inward movement of the stent post 11.

According to the preferred embodiment, the stent posts 11 and connecting brace 13 are fabricated as a single unit from suitable material in suitable dimensions to limit the pivoting of the stent posts 11 about the connecting brace 13 to approximately 10° off of vertical, in the preferred embodiment, so as to minimize tensile stresses in the leaflets 29, 31 and 33. However, the pivot angle may vary in other embodiments depending on the relationship between the height of post 11 above brace 13 and the radial excursion of the top post 11. As will be appreciated from the Figures and the description above, pivoting of the stent posts 11 occurs as a result of twisting or torsional movement of the connecting brace 13. Generally, the amount of pivoting is limited by the expansion of the aorta. Also, the geometry of the valve leaflets prevents pivoting of the stent posts 11 past a certain point (e.g. 15% expansion of commissural diameter), since generated tension limits outward movement of the posts 11. It is contemplated that the rigidity of the stent posts and end stops can be designed to limit pivoting by varying the shape of the cross-section of the stent posts.

Figure 6:
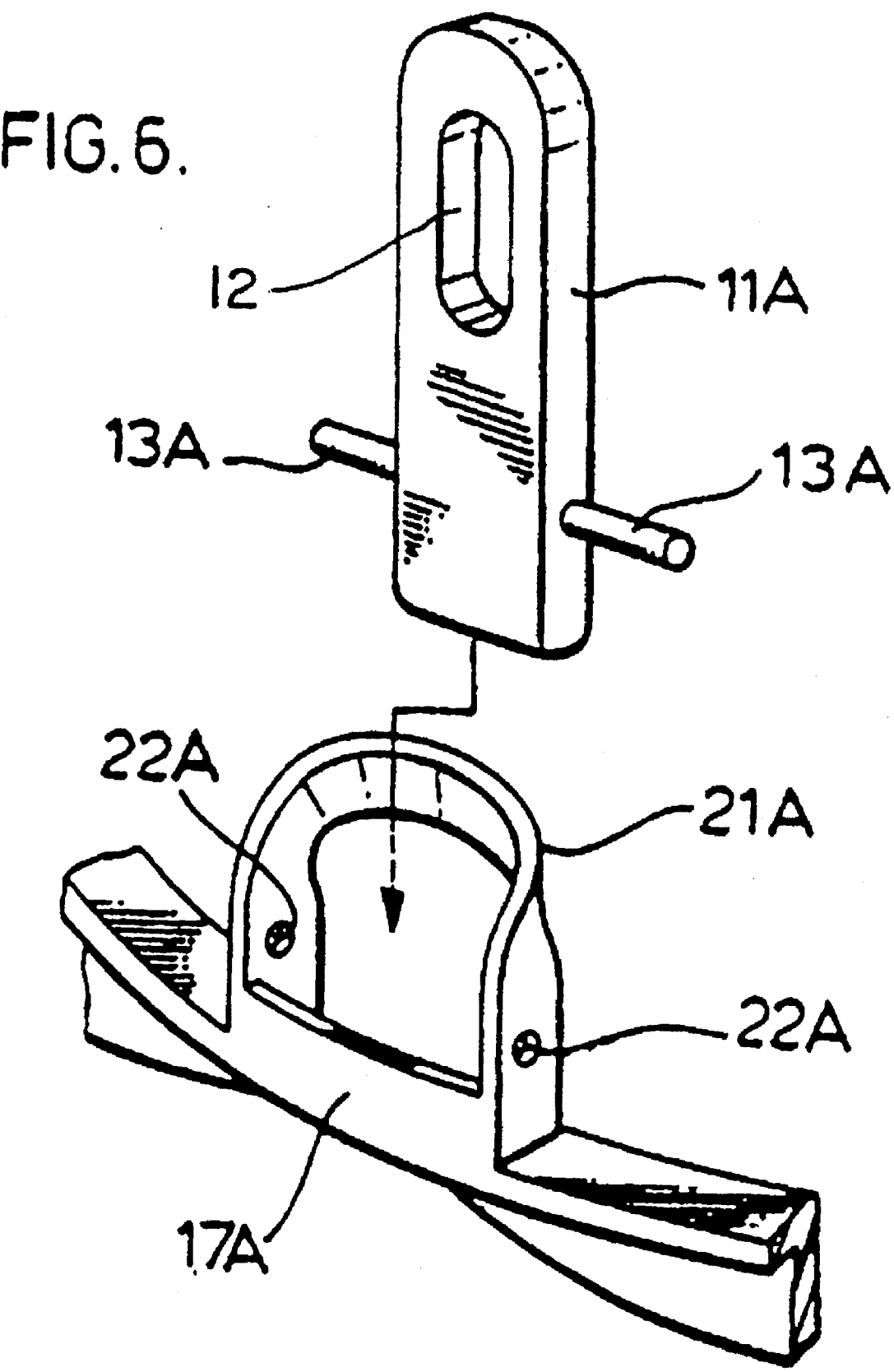
FIG. 6 is a detail in perspective of an alternative embodiment of pivoting post and stop member.

According to the alternative embodiment of FIG. 6, the outward protrusion has been eliminated and the shape of the stop member 17A has been straightened to eliminate the hollow internal portion 19. Also, instead of using a connecting brace, each post 11A is provided with a pair of pivot arms 13A which are received within a respective pair of holes 22A in the stop member 21A.

In summary, whereas prior art heart valves having totally rigid stent posts experience magnitudes of flexural stresses and degrees of bending which are sufficient to produce compressive buckling and leaflet tearing, the valve according to the present invention is characterized by significantly reduced leaflet curvatures and associated stresses. Furthermore, in contrast with prior art bioprosthetic valves in which the stent posts flex inwardly during diastole, the heart valve of the present invention allows for considerable outward pivoting during systole but prevents excessive inward pivoting during diastole in order to reduce the compressive flexural stresses normally associated with the function of existing pericardial bioprosthesis.

Modifications and alternative embodiments of the invention are possible. For example, it is contemplated that human tissue may be used instead of animal tissue for valve 27. Also, the human or animal tissue may be modified in various ways to prevent immune reaction.

Furthermore, as discussed above it is contemplated that the bioprosthetic valve of the present invention may be used to replace other valves in the human body. For example, according to one alternative embodiment, the valve of the present invention may be modified for use in the urinary tract to replace a defective urinary sphincter muscle in order to treat incontinence. Also, the valve may be used in the eye or in the brain to reduce fluid pressure.

All such modifications and embodiments are believed to be with in the sphere and scope of the present invention as defined by the claims appended hereto.

We claim:

1. A bioprosthetic heart valve comprising:
   a) a support ring having three spaced apart end stops projecting upwardly therefrom;
   b) three spaced apart stent posts adapted to pivot outwardly relative to said support ring and to engage respective ones of said end stops for preventing inward pivoting thereof;
   c) leaflet valve means formed from an aortic root and having three generally triangular leaflets defining respective cusps which are adapted to open and close during heart systole and diastole, respectively, said leaflets being joined at respective commissures adjacent said aortic root; and
   d) means for attaching said leaflet valve means to said stent posts and said support ring.

2. The bioprosthetic heart valve of claim 1, wherein said support ring further incorporates a scalloped extension from a bottom surface thereof so as to conform said bottom surface to aortic valve geometry.

3. The bioprosthetic heart valve of claim 1, further comprising a sewing ring circumscribing said leaflet valve means for attaching said leaflet valve means to said support ring.

4. The bioprosthetic heart valve of claim 1, further comprising a cloth covering sewn onto said leaflet valve means.

5. The bioprosthetic heart valve of claim 1, further comprising a cloth covering sewn onto said stent posts.

6. The bioprosthetic heart valve of claim 1, wherein said leaflet valve means consists of one of either animal tissue or human tissue.

7. The bioprosthetic heart valve of claim 6, wherein said animal tissue is chemically treated pig aortic valve.

8. The bioprosthetic heart valve of claim 6, wherein said animal tissue is chemically treated calf pericardium.

9. The bioprosthetic heart valve of claim 1, wherein each of said stent posts has a pair of pivot arms projecting from opposite sides thereof, and wherein each of said end stops includes a pair of holes for receiving respective ones of said pivot arms so as to permit said outward pivoting of said stent posts.

10. The bioprosthetic heart valve of claim 1, wherein the three generally triangular leaflets are arranged in a geometry which prevents the pivoting of the stent posts beyond a 15% expansion of commissural diameter.

11. The bioprosthetic heart valve of claim 1, wherein each of said end stops further comprises a pair of members projecting from said support ring on opposite sides of a respective one of said stent posts for preventing said inward pivoting thereof.

12. A bioprosthetic valve comprising:
   a) a support ring having three spaced apart end stops projecting upwardly therefrom;
   b) three spaced apart stent posts adapted to pivot outwardly relative to said support ring and to engage respective ones of said end stops for preventing inward pivoting thereof;
   c) leaflet valve means having three generally triangular leaflets defining respective cusps which are adapted to open and close; and
   d) means for attaching said leaflet valve means to said stent posts and said support ring.

13. The bioprosthetic heart valve of claim 12, wherein the three generally triangular leaflets are arranged in a geometry which prevents the pivoting of the stent posts beyond a 15% expansion of commissural diameter.

14. A bioprosthetic heart valve comprising:
   a) a support ring having three spaced apart end stops projecting upwardly therefrom;
   b) three spaced apart stent posts adapted to pivot outwardly relative to said support ring and to engage respective ones of said end stops for preventing inward pivoting thereof;
   c) a stent post ring to which said stent posts are pivotally connected for pivoting movement, wherein said stent post ring is adapted to limit said outward pivoting of said stent posts to approximately 10° from vertical;
   d) leaflet valve means formed from an aortic root and having three generally triangular leaflets defining respective cusps which are adapted to open and close during heart systole and diastole, respectively, said leaflets being joined at respective commissures adjacent said aortic root; and
   e) means for attaching said leaflet valve means to said stent posts and said support ring.

15. A bioprosthetic heart valve comprising:
   a) a support ring having three spaced apart end stops projecting upwardly therefrom;
   b) three spaced apart stent posts adapted to pivot outwardly relative to said support ring and to engage respective ones of said end stops for preventing inward pivoting thereof;
   c) a stent post ring to which said stent posts are pivotally connected for pivoting movement;
   d) leaflet valve means formed from an aortic root and having three generally triangular leaflets defining respective cusps which are adapted to open and close during heart systole and diastole, respectively, said leaflets being joined at respective commissures adjacent said aortic root; and
   e) means for attaching said leaflet valve means to said stent posts and said support ring.

16. The bioprosthetic heart valve of claim 15, wherein each of said end stops further comprises a first member projecting from an outer diameter of said support ring, said first member being of generally spherical segment shape defining a hollow internal portion, and a second member projecting from said outer diameter toward an inner diameter of said support ring, said second member extending substantially above said first member and being of generally arcuate shape.

17. The bioprosthetic heart valve of claim 16, wherein each of said stent posts further comprises a main body portion connected to said stent post ring at a pivot point adjacent a lower end of said stent post such that a portion of said main body moves inwardly no further than said second member above said pivot point during diastole, said lower end having an outward protrusion below said pivot point adapted to hook into said hollow internal portion of said first member during diastole, whereby said stent post is prevented from inward pivoting during diastole while said stent post being permitted to pivot outwardly by twisting of said stent post ring during systole.

18. The bioprosthetic heart valve of claim 15, further comprising a wire frame conforming in shape to said respective cusps of said leaflet valve means and connected to an upper end of each of said stent posts, for supporting said leaflet valve means on said stent post ring.

19. The bioprosthetic heart valve of claim 18, wherein said wire frame is received within cooperatively dimensioned slots disposed in the upper end of each of said stent posts.

20. The bioprosthetic heart valve of claim 15, wherein said stent post ring is fabricated from a flexible polymer.

21. The bioprosthetic heart valve of claim 15, wherein the three generally triangular leaflets are arranged in a geometry which prevents the pivoting of the stent posts beyond a 15% expansion of commissural diameter.

* * * * *